United States Patent [19]

Scott et al.

[11] 3,997,419
[45] Dec. 14, 1976

[54] DISSOLVED OXYGEN CELL

[75] Inventors: Timothy F. Scott, Brea; Gordon R. Brushwyler, Anaheim, both of Calif.

[73] Assignee: Robertshaw Controls Company, Richmond, Va.

[22] Filed: June 9, 1975

[21] Appl. No.: 585,030

Related U.S. Application Data

[63] Continuation of Ser. No. 399,374, Sept. 21, 1973, abandoned.

[52] U.S. Cl. .............................. 204/195 P; 324/29
[51] Int. Cl.² ....................................... G01N 27/46
[58] Field of Search ........................ 204/195 P, 1 P

[56] References Cited

UNITED STATES PATENTS

| | | | |
|---|---|---|---|
| 3,133,873 | 5/1964 | Miller et al. | 204/196 |
| 3,235,477 | 2/1966 | Keyser et al. | 204/195 P |
| 3,351,544 | 11/1967 | Medlar | 204/195 P |
| 3,510,421 | 5/1970 | Gealt | 204/195 P |

*Primary Examiner*—T. Tung
*Attorney, Agent, or Firm*—Fulwider, Patton, Rieber, Lee & Utecht

[57] ABSTRACT

An electrochemical device for sensing the concentration of dissolved oxygen in aqueous liquids is described. The device has a housing with a projecting boss that supports an assembly of the cell cathode and a permeable membrane with a removable retainer means overlying peripheral edges of the membrane and with compressive sealing means to permit facile replacement of the membrane and/or cathode. The cell anode is of expanded form in the shape of a coiled metal wire wrapped about a plurality of spaced posts within the cell chamber. Internally of the chamber is a tubular means which projects above the cathode in juxtaposition to the expanded form anode to provide a well about the cathode which is thereby shielded from accumulation of any precipitate that may form in the electrolyte in the proximity of the anode surfaces. The electrochemical system includes an electrolyte of approximately equal molar concentrations of a potassium halide, preferably iodide, and potassium hydroxide which provides maximum sensitivity and operating life. The preferred electrodes are a silver cathode and lead anode which generate a sufficient potential for accurate measurement of dissolved oxygen in aqueous media. The electrodes are connected in the external circuit to a load resistor and the voltage generated across the resistor is applied to a sensitive galvanometer which is calibrated or standardized to dissolved oxygen concentrations. A temperature compensating circuit can also be provided.

14 Claims, 7 Drawing Figures

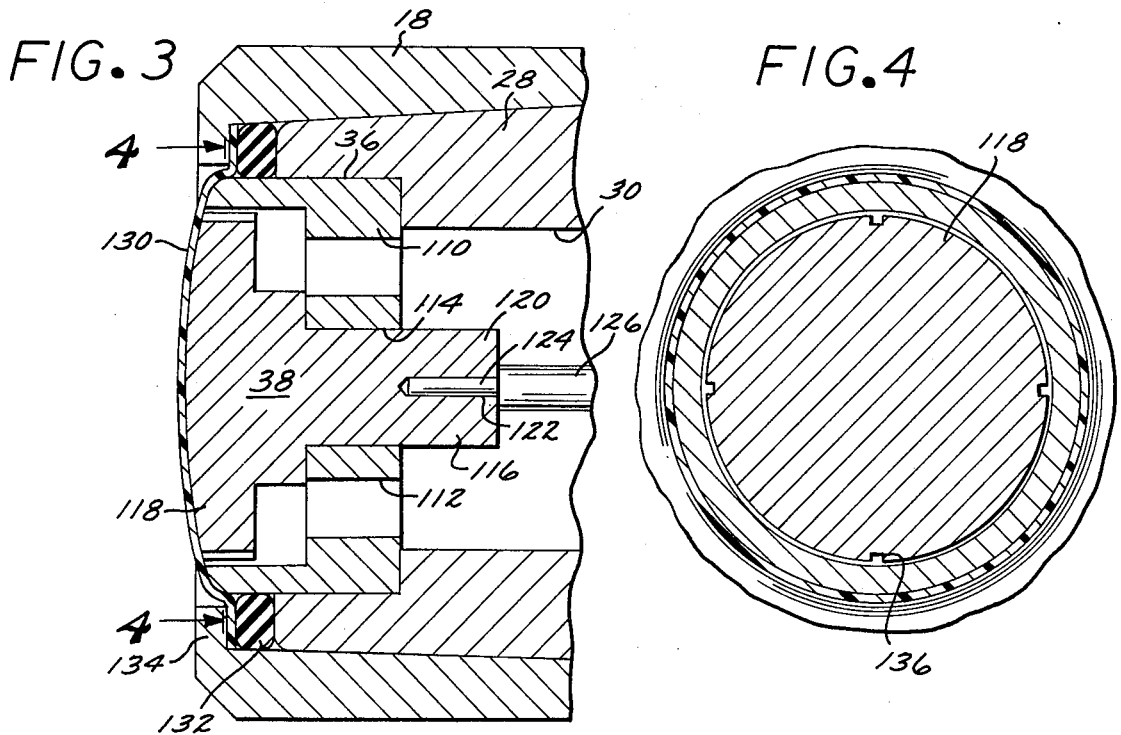
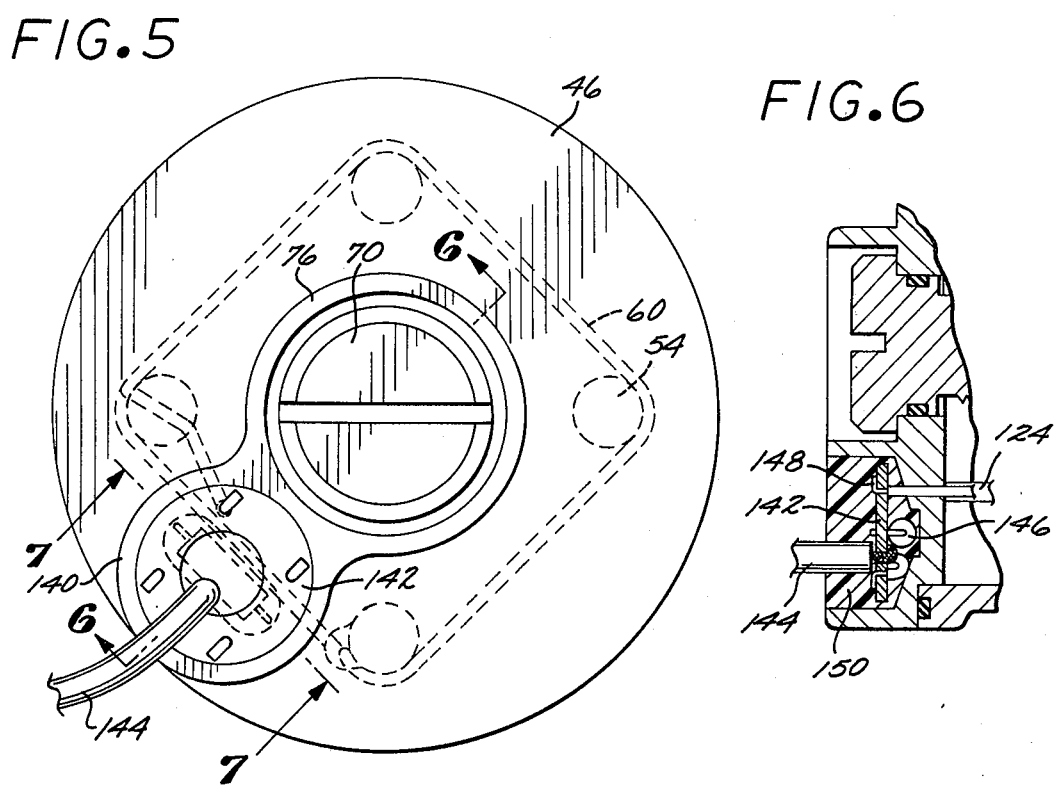

DISSOLVED OXYGEN CELL

CROSS-REFERENCE TO RELATED APPLICATION

The present application is a Continuation of U.S. Ser. No. 399,374, filed Sept. 21, 1973, now abandoned, for DISSOLVED OXYGEN INSTRUMENT. The benefit of the earlier filing date is claimed for the subject matter common to both applications.

BACKGROUND OF THE INVENTION

1. Field of the Invention

In many industrial operations it is desirable to known the dissolved oxygen content of various aqueous streams. To illustrate, the direct measurement of the dissolved oxygen concentration is often needed in control of process variables of industrial aeration treatment of waste effluents. Direct measurement of dissolved oxygen content of surface water and streams is often desired in environmental studies on marine life. In addition, differential measurement of oxygen concentrations of various aqueous media between the inlet and outlet of a flow-through system can be used to monitor the activity of aerobic microbial processes.

Measurements of dissolved oxygen content are often desired at remote sites and it is desirable to have an instrument having a long cell life without need for frequent recalibration or standardization and free from frequent maintenance. Furthermore, what maintenance may be required should be free of mechanical complexity, thereby permitting field servicing of the instrument and obviating the need to return the instrument to a shop.

2. Description of the Prior Art

U.S. Pat. Nos. 2,913,386 and 2,651,612 describe dissolved oxygen analyzing instruments which employ a conductive electrolyte and electrodes of metals having sufficient electromotive dissimilarities to provide electrochemical cells having output voltages which are a function of dissolved oxygen concentration. These instruments are shown to have an oxygen permeable membrane isolating the cell from the liquid being analyzed. The typical reaction of the cells is:

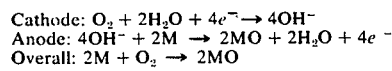

Cathode: $O_2 + 2H_2O + 4e^- \rightarrow 4OH^-$
Anode: $4OH^- + 2M \rightarrow 2MO + 2H_2O + 4e^-$
Overall: $2M + O_2 \rightarrow 2MO$ Typically a noble metal such as silver, platinum, palladiun or gold was used for the cathode and a metal such as copper, lead, nickel, cadium or tin is used for an anode.

A common failing of these dissolved oxygen instruments is their inability to maintain uniform activity over extended periods of use. As indicated in the preceding reaction, the cell operation forms a metal oxide. Metal oxides have relatively low solubility in aqueous media and, accordingly, rapid polarization of the anode by a coating of the insoluble metal oxide can occur. To minimize the requirement for frequent restandardization of the cell, it is desirable that the electrical conductivity through the cell, i.e. through the electrolyte as well as across the electrode-electrolyte interfaces be stable and relatively independent of the reactions occurring at the electrodes. It is, therefore, desirable to provide a cell having an electrolyte in which the metal oxide is relatively soluble to insure removal of the metal oxide from the anode surface before its precipitation. Additionally the electrolyte should have a sufficiently high concentration of mobile, current-conducting ions to provide a high electro-chemical conductivity and thereby insure maximum instrument sensitivity. Heretofore, these electrolyte characteristics have not been optimized and either or both of the electrical conductivity or metal oxide solubility of the electrolyte have been compromised.

When the instrument is used over an extended period of time, the concentration of the metal oxide in the electrolyte reaches its limit of solubility and precipitates of metal oxides are formed. To insure maximum life of the instrument, the electrodes should be protected from becoming covered with the precipitates which are formed in the electrolyte. Since the surface area of the cathode is minimized in these cells, it is particularly critical that the cathode be shielded from such precipitation if operation for extended periods is to be achieved.

The electro-chemical cell is shielded from the liquid under investigation by a protective oxygen-permeable barrier that is located adjacent to the cathode. The barrier is fragile and must be supported by a durable backing to permit its use in liquids which are subjected to pressure surges or which contain suspended solid matter that may strike the membrane. In many prior devices, the cathode and membrane are relatively fragile and are not well suited for such applications. Additionally, a common failing of the prior devices is that the cathode or protective membrane are not readily accessible and their replacement requires extensive shop maintenance The instrument of this invention obviates most of the aforementioned failings of the prior art devices and provides a constant sensitivity of measurement of dissolved oxygen in aqueous media over extended periods of use.

SUMMARY OF THE INVENTION

The oxygen sensing device of this invention comprises a housing having an internal chamber for containing an electrolyte with a boss projecting from one end thereof and having a through opening in the boss with a cathode member mounted in the outboard port of the through opening. An oxygen-permeable membrane overlies the outer surface of the cathode member and is retained in sealed relationship to the outboard port of the through opening by retaining means which overlies the peripheral edges of the membrane and retains these edges against a compressible sealing means in the boss. The retaining means is removably secured to the housing to permit facile replacement of the oxygen-permeable membrane and cathode.

The opposite end of the housing is open and receives, in sealed relationship thereto, an anode-lid assembly that is removably secured to the housing. The anode-lid assembly supports a plurality of coextensive posts in spaced array within the interior chamber of the housing to define an expanded form. The anode in the form of a wire of a metal having an oxidation potential more positive than the metal of the cathode is coiled or wrapped about the expanded form to provide an anode of greatly extended surface area.

Tubular means is provided within the chamber of the housing in a position coaxial with the through opening of the boss and this tubular means projects substantially the entire length of the interior chamber. Near its upper extremity, the tubular chamber bears a radial port to provide communication between its interior and the interior of the chamber within the housing.

The housing chamber is filled with an aqueous solution of approximately equal molar quantities of a potassium halide, preferably potassium iodide and potassium hydroxide. The potassium hydroxide provides a medium which is buffered and, therefore, relatively unaffected by the cathode reaction. Additionally, metal oxides are more soluble in strongly alkaline solutions such as aqueous solutions of potassium hydroxide and, accordingly, this alkaline solution inhibits polarization of the anode by removal of the metal oxide from the anode-electrolyte interface. Precipitates of metal oxide which are formed over the extended life of the instrument will gravitate to the bottom of the housing chamber and are shielded from entrance into the through opening of the boss by the internal tubular menans. The presence of the potassium halide insures a high electrical conductivity of the electrolyte throughout its use and thereby insures that the instrument will maintain a high sensitivty for dissolved oxygen throughout its operating life.

BRIEF DESCRIPTION OF THE DRAWINGS

FIG. 3 is a sectional elevation view of the bottom tip of the instrument showing the cathode assembly and its mounting in the instrument;

FIG. 4 is a view of the cathode assembly taken along section 4—4 of FIG. 3;

FIG. 5 is a view of the top of the instrument;

FIG. 6 is a sectional view taken along line 6—6 of FIG. 5; and

DESCRIPTION OF THE PREFERRED EMBODIMENTS

Figure 1:
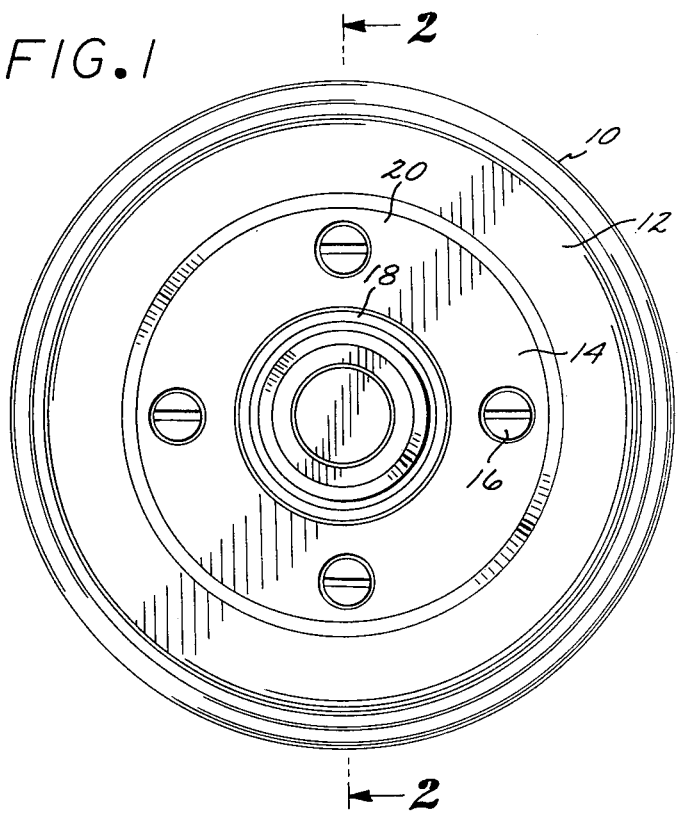
FIG. 1 is a view of the bottom of the instrument.

Referring now to FIG. 1, the instrument is shown as comprising a generally circular housing 10 with a flat undersurface 12 to which is secured retaining means 14 by a plurality of screw fasteners 16 which are spaced about the periphery of the retaining means 14. The retaining means is in the form of a sleeve 18 that bears an annular flange 20 in which screw fasteners 16 are mounted.

Figure 2:
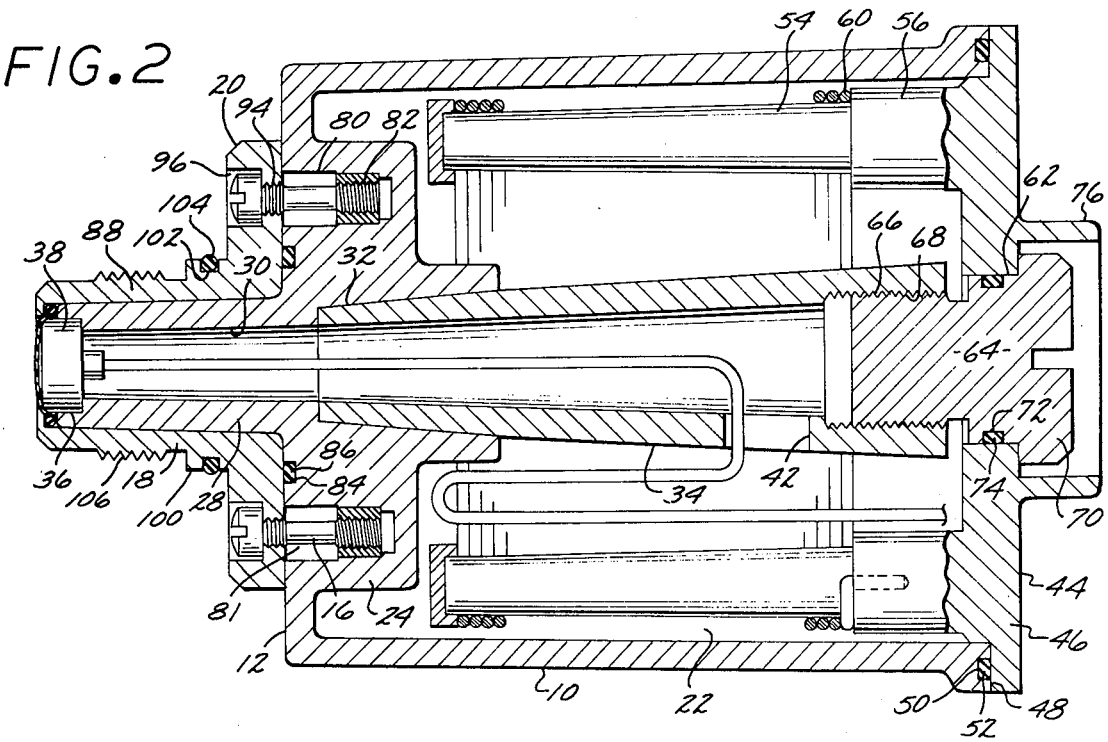
FIG. 2 is an elevation view of the instrument taken along section 2—2 of FIG. 1.

Referring now to FIG. 2, the circular housing 10 can be seen to have an internal chamber 22 with a stepped, annular boss 24 on its inside bottom surface. The under-surface 12 of housing 10 bears a centrally located circular boss 28 that projects a substantial distance beneath the bottom surface 12. A through opening 30 extends the length of boss 28 and the interior end of opening 30 is counter-bored to provide a tapered seat 32 for internal tubular member 34. The outboard port of opening 30 is counter-bored at 36 to provide an annular seat for the cathode assembly 38.

Tubular member 34 is fixedly secured in its tapered seat 32 and is coaxial with through opening 30 in boss 28 to provide a continuous passageway 40 extending from the cathode assembly to the top of the interior chamber 22. At least one port 42 is provided through the wall of tubular member 34 at its upper extremity.

The upper end of housing 10 is open and receives the anode-lid asembly 44. The lid 46 of this assembly has an annular rim 48 which engages against the upper edge of housing 10. This upper edge bears an annular groove 50 in which is seated compressible sealing means such as O-ring 52 to provide a sealable relationship between lid 46 and housing 10.

The undersurface of lid 46 bears a plurality of coextensive posts 54 which project from bosses 56. Posts 54 are generally cylindrical and are positioned in a spaced array about the internal periphery of chamber 22 to provide an expanded form for the anode assembly. The anode of this assembly comprises a helical winding of metal wire or cable 60 which extends the substantial length of posts 54.

Lid 46 has a central aperture 62 in which is mounted plug member 64. The upper end of tubular member 34 is internally threaded at 66 and the lower end of plug 64 bears mating male threads 68 to permit plug 64 to be turned into and secured to tubular member 34. Plug 64 has a head 70 which overlies the annular shoulder about bore 62 so that plug 64 serves as means to removably secure lid 46 to housing 10. The shank of plug 64 bears an annular groove 72 in which is seated a compressible and resilient sealing means such as O-ring 74 that provides a sealed relationship between plug 64 and lid 46, thereby sealing internal chamber 22. In the illustrated, preferred embodiment, the upper surface of lid 46 bears a centrally positioned upright sleeve member 76 that surrounds bore 62 and provides a protective shield about plug 64.

The undersurface 12 of housing 10 bears a plurality of longitudinal bores 80, in each of which is fixedly mounted screw retaining means 82 in the form of an internally threaded sleeve. The undersurface 12 also bears an annular groove 84 surrounding boss 28 in which is mounted a resilient, compressible sealing means in the form of O-ring 86.

Telescopically surrounding boss 28 is retaining means 88 in the form of a sleeve 18 having an annular flat flange 20. Flange 20 bears a plurality of internally threaded holes 94 which are in radial alignment with bores 80 of housing 10. These threaded holes 94 are counter-bored at 96 to provide a countersink for screw fasteners 16 which extend through threaded holes 94 and into threaded engagement with screw retaining means 82. Screw fasteners 16 are captive on retaining means 88 by means of the undercut section 81 of the screws 16 and the internal threads 94 which allow the screws 16 to pass through the flange 20 by turning until reaching the undercut section 81 of screw 16.

The outer surface of sleeve 18 has an annular shoulder 100 that is provided with an annular groove 102 in which is mounted a resilient, compressible sealing means such as O-ring 104. The outer surface of sleeve 18 is also provided with make threads 106 and these threads, together with sealing means 104, permit the instrument to be removably secured, in a sealed relationship, to suitable, threaded access ports of process equipment.

The cathode assembly of the instrument is illustrated in FIG. 3. The cathode assembly 38 is shown seated in counter-bore 36 located at the outboard port of through opening 30 in boss 28. The cathode assembly comprises a collar 110 seated in counterbore 36. The base of collar 100 bears a plurality of through apertures 112 and a central through opening 114. Collar 110 is formed of a suitable insulating material, e.g. a plastic such as Noryl. The cathode, formed of a noble metal, preferably silver, is shown as a plug having a slightly convex head 118 and a central boss 120 which extends, in a pressed fit, through bore 114 of colar 110. Boss 120 is bored at 122 for insertion of the end of electrical connector 124 which can be secured thereto by crimping or compressing the boss about connector 124 after its insertion in bore 122. Connector 124 is covered by electrical insulation wrapping 126 that can be formed of conventional, heat-shrinkable tubing to insure the sealed isolation of electrical connector 124 from the electrolyte within the housing 22.

The oxygen-permeable membrane which is formed of suitable material, typically of plastics such as FEP Teflon, is in the form of a circular disk 130 having a thickness of about 2 mils. This disk overlies the convex head 118 of cathode 116. Disk 130 is of slightly greater diameter than head 118 to provide a peripheral edge which bears against resilient compressible sealing means in the form of an O-ring 132. The end of sleeve 18 bears an annular lip 134 that overlies the peripheral edge of disk 130 and compresses this peripheral edge against O-ring 132 to secure the entire assembly in a sealed relationship. This assembly provides an electrical resistance across the membrane disk 130 which is at least about 200K ohms, thereby insuring the electrical isolation of the cell.

Referring now to FIG. 4, the head 118 of cathode 116 can be seen to have a plurality of longitudinal slots 136 spaced about its periphery. These slots provide for communication of the electrolyte to the surface of cathode 116 and it has been found that an optimum size for such slots is from 0.01 to about 0.03, preferably 0.02 inch.

Referring now to FIG. 5, the upper surface of the anode-lid assembly is shown. The upper surface of lid 46 is generally flat with the centrally positioned, generally circular wall 76 contiguous with a second cylindrical wall 140. The upper surface of plug 70 is shown within the cavity defined by wall 76 while the cavity within circular wall 140 provides a housing for mounting of circuit board 142 that supports the electrical connections to external lead 144 of the instrument. The arrangement of the expanded form anode assembly comprising posts 54 that are positioned in a spaced array about the chamber 22 and the anode wire 60 can be seen in the broken lines appearing in FIG. 5.

Figure 7:
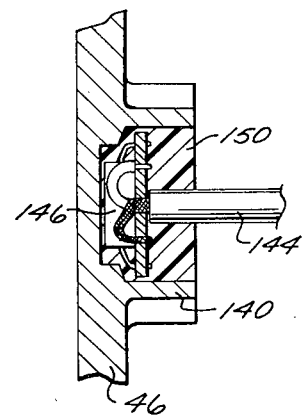
FIG. 7 is a sectional view taken along line 7—7 of FIG. 5 illustrating the electrical lead connections of the instrument.

Referring now to FIGS. 6 and 7, the circuit board 142 supports on its undersurface a resistor 146 of suitable value, e.g. from 1000 to about 50,000 ohms, preferably 10,000 ohms, and the connections for the electrical connector 148 which extends to the anode 60 and electrical connector 124 which extends to the cathode. The anode and cathode electrical connectors are connected to the terminals of resistor 146 and the ends of the two-wire electrical lead 144 from the instrument are also connected across this resistor. The entire cavity within sleeve 140 is filled with a potting compound 150 to isolate the electrical connections and components from environmental weathering.

As previously mentioned, the preferred metal for the cathode is silver. Chemically pure lead wire is the preferred metal for the anode. The electrolyte which is used with these electrodes comprises a substantially equal molar mixture of a potassium halide, preferably potassium iodide and potassium hydroxide. These solutes can be employed in molar proportions from 1:2 to 2:1 parts potassium iodide per parts of potassium hydroxide. The concentration of each of these solutes in the electrolyte can be from about 0.5 to about 2 molar, preferably the concentration of each being one molar. It has been found that the approximately equal molar proportions of potassium iodide and potassium hydroxide provide maximum sensitivity and stability of the instrument over extended periods of use. The potassium hydroxide serves as a buffer to avoid pH swings of the electrolyte when fluids having widely varied dissolved oxygen contents are under investigation for long periods of time. The potassium hydroxide also provides for maximum solubility of the lead oxide which is formed by the electro-chemical reaction at the anode. The potassium iodide provides a highly mobile, electrically conducting ion species within the electrolyte so that the electrolyte provides a desirably high electrical conductivity between the cathode and anode insuring maximum sensitivity of the instrument for dissolved oxygen contents.

The operational features of the instrument are relatively apparent from the illustration and preceding description. During operation of the cell, lead oxide reaches its saturation level in the electrolyte and continued operation results in precipitation of the lead oxide. This precipitation does not, however, interfere with the operation of the cell since any precipitates which are formed gravitate to the bottom of chamber 22. The precipitates are precluded from depositing on the surface of the cathode by tubular member 34 which extends coaxially with and above through passageway 30. Precipitation of the lead oxide which occurs will be in the vicinity of the annular or helical anode 60 and such precipitates will, therefore, not enter the internal passageway of tubular member 34.

The cathode assembly is readily accessible for maintenance and servicing. The retainer 88 can be readily removed from its telescoping and sealing engagement about boss 28 by loosening screw fasteners 16 and the retainer can then be dropped from housing 10. This exposes the entire cathode assembly and the assembly can be pulled from its pressed fit in counterbore 36 for replacement. Similarly, the removal of retainer 88 will expose the circular disk 130 so that the latter can be readily replaced without disturbing the remaining components of the intrument.

When the anode is to be serviced, plug 64 can be retracted from its threaded engagement with tubular member 34 and the anode-lid assembly can be removed from the housing. To permit lifting of the lid assembly from housing 10, the electrical connector 124 which extends to cathode assembly 38 is looped within chamber 22 in the manner shown in FIG. 1 and passes through port 42 into tubular member 34. The removal of the anode-lid assembly 44 exposes the entire expanded form anode for servicing.

Routine servicing of the electrolyte is readily accomplished simply by removing plug 64. Additional electrolyte may then be added to chamber 22 through central port 62.

As illustrated in the preferred embodiment, the invention provides a rugged instrument which can be readily serviced in the field for replacement of all of the components of the instrument cell. Long operational life of the instrument is insured by the electrolyte composition and by the internal construction and configuration of the anode assembly and the protective well in the form of tubular member 34. The use of a telescoping retaining means that is secured by screw fasteners to the body insures that no damage of the oxygen-permeable membrane will occur when the retaining means is compressed against the oxygen-permeable membrane 130 and the annular seal 132, This, also, provides for simple field servicing of the instrument.

The invention has been described with reference to the presently preferred and illustrated embodiment. It is not intended that the invention be unduly limited by such illustration. Instead, it is intended that the invention be defined by the elements and reagents, and their obvious equivalents, set forth in the following claims.

What is claimed is:

1. An oxygen sensing apparatus comprising:
   a housing bearing a projecting boss extending from one end thereof with a through opening extending through said boss and terminating in a sealing edge;
   a lid removably and sealably engaged to the opposite end of said housing to define a chamber therein;
   spaced apart electrode means in said apparatus comprising anode means within said housing and a cathode assembly removably seated in the outboard end of said through opening and including collar means removably seated in said through opening and having a central bore and a plurality of apertures in fluid communicatiion with said through opening and a cathode plug having a central boss seated in said bore and a cathode head received in the outboard end of said collar means and surrounded by said sealing edge;
   barrier means in the form of an oxygen-permeable membrane overlying said cathode plug and having its peripheral edges turned back over said sealing edge;
   retaining means telescopically overfitting said boss and formed with an inturned rim overlying the peripheral edges of said membrane;
   compressible sealing means for sealing said membrane against said sealing edge; and
   mounting means mounting said retaining means on said housing and operative to compress said inturned rim against said sealing edge;
   whereby said cathode assembly is removable from said through opening through said outboard end by detaching said retaining means.

2. An oxygen sensing apparatus according to claim 1 wherein:
   said housing includes a plurality of spacedapart coextensive posts projecting into said chamber to define an expanded form; and
   said anode means includes lead wire means wrapped around said posts.

3. An oxygen sensing apparatus according to claim 1 wherein:
   said retaining means is formed with a sleeve receiving said projecting boss; and
   fastening means for drawing said retaining means down on said housing to seal said membrane against said sealing edge.

4. The oxygen sensing apparatus according to claim 1 wherein:
   said housing bears an electrical conductor extending through said through opening and into electrical connection to said central boss of said cathode plug.

5. The oxygen sensing apparatus according to claim 1 wherein:
   said head of said cathode plug bears a plurality of longitudnal slots about its periphery.

6. Sensing apparatus for sensing a component included in a constituent and comprising:
   a housing formed with an electrolyte chamber having an opening therein, said opening having a sealing edge formed therearound;
   anode means mounted in said chamber;
   a cathode assembly removably mounted in the outside end of said opening in spaced relationship with said anode means including collar means removably seated in said through opening and having a central bore and a plurality of apertures communicating with said chamber and a cathode plug having a central boss seated in said central bore and a head received in the outboard end of said collar means and surrounded by said sealing edge;
   membrane means overlying said cathode assembly and formed with marginal edges overlying said sealing edge;
   a retainer surrounding said opening and formed with a retaining rim bearing holes projecting over said sealing surface, said retainer being telescopically seated on said housing to press said membrane into sealing engagement with said sealing edge; and
   fastening mans extending through said holes and fastening said retainer to said housing and operable to draw said retainer telescopically toward said sealing surface to seal said membrane means against said sealing surface;
   whereby said cathode assembly is removable from said through opening through said outboard end by detaching said retainer.

7. Sensing apparatus according to claim 6 wherein:
   said housing is formed with threaded bores disposed about said opening;
   said retainer is formed with fastening bores aligned with said threaded bores; and
   said fastening means includes threaded studs extending through said fastening bores and screwed into said threaded bores to draw said retainer into sealing position against said membrane means.

8. An oxygen sensing apparatus comprising:
   a housing bearing a projecting boss extending from a central position of its undersurface with a through opening extending through said boss;
   a removable lid sealably engaging the upper end of said housing to define an enclosed chamber therein;
   an expanded form anode in the peripheral regions of the interior of said housing;
   a cathode assembly removably seated in the outboard end of said through opening including collar means removably seated in said through opening and having a central bore and a plurality of apertures communicating interiorly of said housing and a cathode plug having a central boss seated in said central bore and a cathode head supported at the outboard end of said collar means;
   oxygen-permeable barrier means overlying said cathode head;
   retaining means removably mounted on the exterior of said boss and sealably engaging said barrier means across the outboard end of said through opening;
   tubular means coaxial with and projecting inwardly from said through opening to an upper region of said housing with port means adjacent its upper end to provide a passageway between its interior and the chamber of the housing; and
   an electrolyte within said housing and electrical conductors extending from said cathode and anode to the exterior of said housing.

9. Sensing apparatus according to claim 8 wherein:
said housing is formed with threaded bores disposed about said opening;
said retaining means is formed with fastening bores aligned with said threaded bores and includes threaded studs extending through said fastening bores and screwed into said threaded bores to draw said retaining means into sealing position against said oxygen permeable barrier means.

10. An oxygen sensing apparatus comprising:
a housing bearing a projecting boss extending from a central position of its undersurface with a through opening extending through said boss;
a removable lid sealably engaging the upper end of said housing;
an anode in the peripheral regions of the interior of said housing;
a cathode seated in the outboard end of said through opening;
oxygen-permeable barrier means overlying said cathode;
tubular means coaxial with and projecting inwardly from said through opening to an upper region of said housing with port means adjacent its upper end to provide a passageway between its interior and the interior of the housing; and an electrolyte within said housing and electrical conductors extending from said cathode and anode to the exterior of said housing.

11. An oxygen sensing apparatus according to claim 10 wherein said anode is an expanded form anode.

12. An oxygen sensing apparatus according to claim 11 including retaining means sealably engaging said barrier means across the outboard end of said through opening.

13. An oxygen sensing apparatus according to claim 12 wherein:
said lid bears, projecting from its undersurface, a plurality of coextensive posts and said expanded form anode comprises a continuous metal wire wrapped about said posts.

14. An oxygen sensing apparatus according to claim 10 wherein said cathode comprises an assembly removably seated in the outboard end of said through opening including collar means removably seated in said opening and having a central bore and a plurality of apertures in fluid communication with said through opening and a cathode plug having a central boss seated in said bore and a cathode head seated in the outboard end of said collar means.

* * * * *